United States Patent [19]

Tanabe et al.

[11] Patent Number: 5,723,455
[45] Date of Patent: Mar. 3, 1998

[54] ANTIANDROGENIC AGENTS AND RELATED PHARMACEUTICAL COMPOSITIONS AND METHODS OF USE

[75] Inventors: Masato Tanabe, Palo Alto; Wan-Ru Chao, Sunnyvale; Wesley K. M. Chong, Encinitas; David F. Crowe, Fresno, all of Calif.

[73] Assignee: SRI International, Menlo Park, Calif.

[21] Appl. No.: 815,311

[22] Filed: Mar. 11, 1997

Related U.S. Application Data

[63] Continuation of Ser. No. 177,899, Jan. 6, 1994, abandoned.

[51] Int. Cl.$^6$ .............. C07J 71/00; C07J 1/00; A61K 31/58; A61K 31/565
[52] U.S. Cl. .............. 514/169; 514/172; 514/173; 514/174; 514/176; 514/177; 514/178; 514/182; 540/6; 540/23; 540/31; 540/45; 540/51; 552/502; 552/508; 552/540; 552/544; 552/548; 552/552; 552/553; 552/555; 552/557; 552/559; 552/582; 552/592; 552/596; 552/598; 552/599; 552/603; 552/604; 552/607; 552/608; 552/609; 552/610; 552/611; 552/612; 552/632; 552/633; 552/634; 552/635; 552/638; 552/639; 552/640; 552/641; 552/642; 552/643; 552/646; 552/648; 552/649; 552/650; 552/651; 552/652
[58] Field of Search .............. 540/6, 23, 31, 540/45, 51; 514/169, 172, 173, 174, 176, 177, 178, 182; 552/502, 508, 540, 544, 548, 552, 553, 555, 557, 559, 582, 592, 596, 598, 599, 603, 604, 607, 608, 609, 610, 611, 612, 632, 633, 634, 635, 638, 639, 640, 641, 642, 643, 646, 648, 649, 650, 651, 652

[56] References Cited

U.S. PATENT DOCUMENTS

| | | |
|---|---|---|
| 4,150,127 | 4/1979 | Anner et al. |
| 4,412,993 | 11/1983 | Sokolowski |
| 4,456,600 | 6/1984 | Wiechert et al. |
| 4,558,041 | 12/1985 | Wiechert et al. |
| 4,673,673 | 6/1987 | Laurent et al. |
| 4,874,754 | 10/1989 | Nique et al. |
| 4,891,365 | 1/1990 | Wiechert et al. |
| 4,892,867 | 1/1990 | Wiechert et al. |

FOREIGN PATENT DOCUMENTS

| | | |
|---|---|---|
| 205170 | 12/1983 | Germany |
| 1045235 | 10/1966 | United Kingdom |

OTHER PUBLICATIONS

G. Ohta et al., "Investigations on Steroids. IV. Syntheses of Androstano[2,3–c]–furazans and Related Compounds", *Chem. Pharm. Bull.* 13:1445–1459 (1965).

Ferrari et al, "Endocrine Profile of Topterone, a Topical Antiandrogen, in Three Species of Laboratory Animals", *Meth and Find Exptl Clin Pharmacol* 2(2):65–69 (1980).

R.A. Edgren et al., "Biological Effects of Synthetic Gonanes," *Recent Progress in Hormone Research* (1966) 22:305–341.

S. Nakajin et al., "Inhibitory Effect and Interaction of Stanozolol with Pig Testicular Cytochrome P-450 ($17\alpha$–Hydroxylase/$C_{17,20}$–Lyase)," *Chem. Pharm. Bull.* (1989) 37(7):1855–1858

T. Ojasoo et al., "Towards the Mapping of the Progesterone and Androgen Receptors," *J. Steroid Biochem.* (1987) 27(1–3):255–269.

L.L. Smith, "Absorption Spectra of Substituted $\Delta^4$–3–Ketosteroids in Concentrated sulfuric Acid. III. 19–Nor Series," *Tex. Reports Biol. Med.* (1966) 24(4):674–692.

C.H. Spilman et al. "Relationship between Progesterone Receptor Binding and Progestin Biological Activity," *J. Steroid Biochem.* (1985) 22(3):289–292.

K. Tanayama et al. "Disposition and Metabolism of $16\beta$–Ethyl–$17\beta$–Hydroxy–4–Estren–3–One (TSAA–291), a New Antiandrogen, in Rats," *Steroids* (1979) 65–83.

K. Ueno et al. "Investigation on Steroids. VIII. Synthesis of steroidal [2,3–c]furazans of Pregnane Series," *Chem. Pharm. Bull.* (1967) 15(4):523–527.

*Primary Examiner*—Kimberly J. Prior
*Attorney, Agent, or Firm*—Dianne E. Reed; Bozicevic & Reed LLP

[57] ABSTRACT

Novel antiandrogenic agents are provided. An exemplary group of compounds has the structural formula (I)

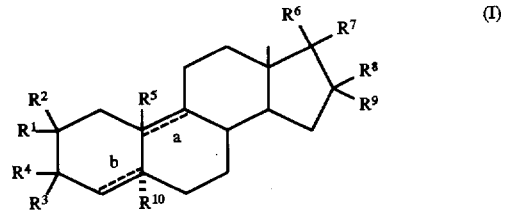

wherein $R^1$ through $R^{10}$, a and b are as defined herein. Pharmaceutical compositions and methods for using the compounds of formula (I) to treat androgen-related clinical conditions are provided, as are methods and compositions for using the compounds as contraceptive agents.

22 Claims, 1 Drawing Sheet

ANTIANDROGENIC AGENTS AND RELATED PHARMACEUTICAL COMPOSITIONS AND METHODS OF USE

The present application is a continuation of application Ser. No. 08/177,899, filed Jan. 6, 1994, now abandoned.

ACKNOWLEDGEMENT OF GOVERNMENT SUPPORT

The present invention was funded in part by the National Institutes of Health under Grant No. AM33747-03; accordingly, the United States Government may have certain rights in the invention.

TECHNICAL FIELD

The present invention relates generally to steroid hormones, and more specifically relates to novel compounds useful as antiandrogenic agents. The invention additionally relates to methods for treating clinical conditions that are either androgen responsive or associated with androgen excess, and to pharmaceutical compositions for treating such clinical conditions. The invention further relates to the use of the novel compounds as male contraceptive agents.

BACKGROUND

Antiandrogenic agents are useful in the treatment of clinical conditions that are either androgen-responsive or associated with androgen excess, such as prostate carcinoma, benign prostatic hyperplasia (BPH), acne, seborrhea, alopecia, hirsutism, polycystic ovarian disease, and male pattern baldness. Antiandrogen therapy can be directed toward any of the regulatory steps in androgen production or action. The control of androgen production in the testis is directly mediated by hypothalamic-pituitary peptide hormones. Neurons of the hypothalamus secrete gonadotropin-releasing hormone (LHRH), a decapeptide that subsequently interacts with high-affinity cell surface receptor sites on the plasma membrane of pituitary cells. LHRH stimulates the release of both luteinizing hormone (LH) and follicle-stimulating hormone (FSH) by a calcium-dependent mechanism.

LH secretion is controlled by the action of androgens and estrogens on the hypothalamus and pituitary. The control of LH in men occurs primarily by negative feedback since testicular steroids inhibit LH secretion. Both testosterone and estradiol can inhibit LH secretion. Although testosterone can be converted to estradiol in the brain and pituitary, the two hormones probably act independently. Testosterone acts on the central nervous system (CNS) to slow the hypothalamic pulse-generator and consequently decreases the frequency of LH pulsatile secretion. In addition, testosterone appears to have negative feedback on LH secretion in the pituitary.

LH reaches the testis via the peripheral circulation, where it interacts with specific high-affinity cell surface receptors on the plasma membranes of the Leydig cells. The binding of LH to its receptor stimulates biosynthesis of testosterone.

Although testosterone is the major secretory product, dihydrotestosterone (DHT), androsterone, androstenedione, progesterone, and 17-hydroxyprogesterone are also secreted by the testis.

In peripheral tissues, testosterone may act directly (e.g., in the CNS, skeletal muscle, and seminiferous epithelium), or serve as a circulating prohormone for the formation of DHT (e.g., prostate) and estrogen. In the prostate, testosterone diffuses into the cell, where it is reduced by 5-alpha reductase to DHT. Ninety percent of total prostatic androgen is in the form of DHT, principally derived from testicular androgens. The remaining 10% of the prostatic androgens are produced in the adrenal glands. Inside the cells of the prostate, both testosterone and DHT bind to the same high-affinity androgen-receptor protein. The hormone-receptor complex then binds to specific DNA binding sites in the nucleus of prostatic cells. This results in increased transcription of androgen-dependent genes and ultimately stimulation of protein synthesis. Conversely, androgen withdrawal from androgen-sensitive tissues results in a decrease in protein synthesis, tissue involution, and in some cases, cell death.

As noted above, a number of physiological problems are associated with androgen production. The most pressing of these at the present time is prostatic cancer, which is a leading cause of cancer in men, with on the order of 100,000 cases diagnosed and 26,000 deaths annually. The androgen dependence of some prostate cancers has been well-established and the primary therapy for metastatic prostate cancer involves androgen suppression. Androgen suppression can be achieved by: removal of the testis, the primary source of androgens, by orchiectomy; inhibition of testicular steroidogenesis at the pituitary level by either luteinizing hormone-releasing hormone analogs or estrogens; inhibition of testicular steroidogenesis at the testicular level using enzyme inhibitors; or inhibition of androgen action by androgen receptor antagonists.

Another important therapeutic area related to androgen production and action is the treatment of benign prostatic hyperplasia, a major problem in the aging human male (and a precursor to prostate cancer in about half of the cases diagnosed), with approximately 400,000 prostatectomies performed annually in the U.S. alone. Although surgery presently represents the most accepted treatment for BPH, several pharmacological approaches have been tested as well. However, no drug therapy has yet proven satisfactory.

Known antiandrogenic agents work by several mechanisms. There are those drugs which inhibit pituitary LH secretion and decrease testosterone and DHT production; these are termed "LHRH agonists," and include, for example, nafarelin, leuprolide, goserelin and buserelin. There are additional drugs which, similarly, inhibit pituitary LH secretion and decrease testosterone and DHT production, but also inhibit androgen receptors; these are drugs such as cyproterone acetate, zanoterone ("WIN®49,596," available from Sterling Winthrop) and the progestins, such as megestrol acetate, hydroxy-progesterone caproate and medrogestone, which exert their antiandrogenic effect through a negative feedback process. Other antiandrogenic drugs include the nonsteroidal agents hydroxyflutamide, Casodex®, and nilutamide which are androgen receptor inhibitors, and 5-alpha-reductase inhibitors (e.g., finasteride), which decreases DHT selectivity. Structures of the representative antiandrogenic agents cyproterone acetate, Casodex®, hydroxyflutamide (a flutamide metabolite) and WIN®49,596 are as follows:

CYPROTERONE ACETATE

CASODEX®

HYDROXYFLUTAMIDE

WIN® 49,596

The currently available antiandrogenic agents, however, are associated with a wide range of problems. For example, known antiandrogens give rise to a number of side effects, including impotence, loss of libido, gynecomastia, heat intolerance, and hot flashes, among others. Some drugs have even been associated with fatal hepatotoxicity (see, e.g., D. K. Wysowski et al., *Ann. Int. Med.* 118(11):860–864 (1993)). Additionally, the known drugs tend to have a very short half-life, necessitating more frequent and/or higher dosages.

The present invention is addressed to the aforementioned need in the art, and is premised on the discovery that certain novel 17-substituted steroids are useful as antiandrogenic agents, at relatively low doses, without causing the problems associated with the antiandrogenic compounds of the prior art. The novel compounds are thus useful for treating clinical conditions that are androgen-responsive and/or associated with androgen production, without giving rise to unwanted side effects as described above. The compounds are thus useful in the treatment of prostate carcinoma, benign prostatic hyperplasia, acne, seborrhea, alopecia, hirsutism, polycystic ovarian disease, and male pattern baldness. The compounds are additionally useful as male contraceptive agents. While not wishing to be bound by theory, the inventors herein postulate that the majority of these new agents appear to act as competitive androgen receptor antagonists by inhibiting prostate growth stimulated by exogenous testosterone, and are essentially devoid of progestational as well as agonist androgenic activity.

BACKGROUND ART

The following references relate to known antiandrogenic compounds and/or to molecular structures which are related in some way to the novel drugs described herein: U.S. Pat. No. 4,150,127 to Anner et al., which describes 19-oxygenated spiroxane-type steroids stated to be useful as diuretic agents; U.S. Pat. No. 4,412,993 to Sokolowski, which describes 7α-methyltestosterones stated to be useful in the treatment of pseudopregnancy, galactorrhea and mastitis in mammals; U.S. Pat. No. 4,673,673 to Laurent et al., which describes 17α-alkyl-17β-hydroxy-1α-methyl-4-androsten-3-ones as antiandrogenic agents; U.S. Pat. No. 4,874,754 to Nique et al., which describes certain 19-nor steroids as contraceptive agents or for the treatment of certain gynecological disorders; and U.S. Pat. No. 4,891,365 to Wiechert et al., which describes certain 17-substituted estradienes and estratrienes for the treatment of gynecological disorders. U.S. Pat. Nos. 4,456,600, 4,558,041, and 4,892,867, all to Wiechert et al., describe 17α-substituted steroids, all of which are stated to be antiandrogenic agents useful for the treatment of acne, seborrhea, alopecia and hirsutism. Additionally, G. Ohta et al., "Investigations on Steroids. IV. Syntheses of Androstano[2,3-c]-furazans and Related Compounds", *Chem. Pharm. Bull.* 13:1445–1459 (1965), and Ferrari et al., "Endocrine Profile of Topterone, a Topical Antiandrogen, in Three Species of Laboratory Animals", *Meth and Find Exptl Clin Pharmacol* 2(2):65–69 (1980), are of interest as directed to related steroid structures.

SUMMARY OF THE INVENTION

Accordingly, it is a primary object of the invention to address the above-mentioned need in the art by providing novel compounds useful as antiandrogenic agents.

It is another object of the invention to provide pharmaceutical compositions for treating clinical conditions that are either androgen responsive or associated with androgen excess.

It is still another object of the invention to provide pharmaceutical compositions for use as male contraceptive agents.

It is yet another object of the invention to provide a method for treating clinical conditions that are either androgen responsive or associated with androgen excess.

It is a further object of the invention to provide such a method which involves oral administration of a compound as described herein, at an antiandro-genically effective dosage.

It is still a further object of the invention to provide a contraceptive method which involves orally administering a compound as described herein to a fertile mammalian male within the context of a predetermined dosing regimen.

Additional objects, advantages and novel features of the invention will be set forth in part in the description which follows, and in part will become apparent to those skilled in the art upon examination of the following, or may be learned by practice of the invention.

In one embodiment, the invention relates to methods of using compounds having the structural formula (I)

(I)

as antiandrogenic and/or contraceptive agents, within the context of a dosing regimen effective to achieve the desired intended result. In formula (I):

$R^1$ and $R^2$ are independently selected from the group consisting of hydrogen and lower alkyl, and $R^3$ and $R^4$ are independently selected from the group consisting of hydrogen, hydroxyl, and lower alkoxy or they may together represent a single carbonyl group, with the proviso that if one of $R^3$ and $R^4$ is hydroxyl or lower alkoxy, the other is hydrogen;

alternatively, one of $R^1$ and $R^2$ may be linked to one of $R^3$ and $R^4$ to provide a ring;

$R^5$ is hydrogen or lower alkyl, unless "a" represents a double bond, in which case it is nil;

$R^6$ and $R^7$ are independently selected from the group consisting of hydrogen, hydroxyl and lower alkyl, or they may together represent a single carbonyl group or be linked to provide a cycloalkyl or cyclooxyalkyl ring containing 3 to 6 carbon atoms;

$R^8$ and $R^9$ are independently selected from the group consisting of hydrogen and lower alkyl;

$R^{10}$ is hydrogen, unless "b" represents a double bond, in which case it is nil; and a and b represent optional double bonds.

The invention also relates to pharmaceutical compositions containing one or more compounds of structural formula (I), and further relates to certain novel compounds encompassed by formula (I), as will be explained in detail below.

DETAILED DESCRIPTION OF THE INVENTION

Definitions and Nomenclature

Before the present compounds, compositions and methods are disclosed and described, it is to be understood that this invention is not limited to specific reagents or reaction conditions, specific pharmaceutical carriers, or to particular administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an antiandrogenic agent" includes mixtures of antiandrogenic agents, reference to "a pharmaceutical carrier" includes mixtures of two or more such carriers, and the like.

In this specification and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, preferably one to four carbon atoms. The term "cycloalkyl" intends a cyclic alkyl group, typically of 3 to 6 carbon atoms, more preferably 4 to 5 carbon atoms. The term "cyclooxyalkyl" intends a cyclic alkyl group containing a single ether linkage, again, typically containing 3 to 6 carbon atoms, more preferably 4 to 5 carbon atoms.

The term "alkenylene" refers to a difunctional branched or unbranched hydrocarbon chain containing from 2 to 24 carbon atoms and at least one double bond. "Lower alkenylene" refers to an alkenylene group of 2 to 6, more preferably 2 to 5, carbon atoms.

The term "aryl" as used herein refers to a monocyclic aromatic species of 5 to 7 carbon atoms, and is typically phenyl. Optionally, these groups are substituted with one to four, more preferably one to two, lower alkyl, lower alkoxy, hydroxy, and/or nitro substituents.

"Halo" or "halogen" refers to fluoro, chloro, bromo or iodo, and usually relates to halo substitution for a hydrogen atom in an organic compound. Of the halos, chloro and fluoro are generally preferred.

"Optional" or "optionally" means that the subsequently described event or circumstance may or may not occur, and that the description includes instances where said event or circumstance occurs and instances where it does not. For example, the phrase "optionally present double bond" means that a double bond may or may not be present and that the description includes both the instance where a double bond is present and the instance where it is not. A dotted line adjacent an unbroken line which is stated to indicate an "optional double bond" accordingly means that a double bond may or may not be present (and if not present, that the adjacent atoms are covalently bound via a single bond).

By the term "effective amount" or "antiandrogenically effective amount" of an agent as provided herein is meant a nontoxic but sufficient amount of the agent to provide the desired antiandrogenic effect. As will be pointed out below, the exact amount required will vary from subject to subject, depending on the species, age, and general condition of the subject, the severity of the condition being treated, and the particular antiandrogenic agent and its mode of administration, and the like. Thus, it is not possible to specify an exact "effective amount." However, an appropriate effective amount may be determined by one of ordinary skill in the art using only routine experimentation.

By "pharmaceutically acceptable" is meant a material which is not biologically or otherwise undesirable, i.e., the material may be administered to an individual along with the selected antiandrogenic agent without causing any undesirable biological effects or interacting in a deleterious manner with any of the other components of the pharmaceutical composition in which it is contained.

In describing the location of groups and substituents, the following numbering systems will be employed.

This system is intended to conform the numbering of the cyclopentanophenanthrene nucleus to the convention used by the IUPAC or Chemical Abstracts Service. The term "steroid" as used herein is intended to mean compounds having the aforementioned cyclopentanophenanthrene nucleus.

In these structures, the use of bold and dashed lines to denote particular conformation of groups again follows the IUPAC steroid-naming convention. The symbols "α" and "β" indicate the specific stereochemical configuration of a substituent at an asymmetric carbon atom in a chemical structure as drawn. Thus "α," denoted by a broken line, indicates that the group in question is below the general plane of the molecule as drawn, and "β," denoted by a bold line, indicates that the group at the position in question is above the general plane of the molecule as drawn.

In addition, the five- and six-membered rings of the steroid molecule are often designated A, B, C and D as shown.

The Novel Compounds

The novel compounds provided herein are those defined by structural formula (I), above, wherein $R^1$ through $R^{10}$, a and b are as defined earlier herein, with the provisos that: (1) when one of $R^1$ and $R^2$ are linked to one of $R^3$ and $R^4$ to provide a ring, neither $R^6$ nor $R^7$ is hydroxyl; and (2) when $R^3$ and $R^4$ together represent a single carbonyl group, $R^5$ is hydrogen and "a" is nil. Preferred compounds encompassed by formula (I) fall within two groups, as follows.

The first group of compounds may be represented by structural formula (II):

In this subset of compounds, $R^1$ and $R^2$ are independently selected from the group consisting of hydrogen and lower alkyl, and $R^6$, $R^7$, $R^8$ and $R^9$ are as defined above with respect to Formula (I). An example of a particularly preferred compound within this subset has the structural formula (II-1):

The second group of compounds may be represented by structural formula (III):

In this subset of compounds, $R^5$ is either hydrogen or lower alkyl, and $R^6$, $R^7$, $R^8$ and $R^9$ are as defined above with respect to Formula (I). An example of a particularly preferred compound within this subset has the structural formula (III-1):

Other examples of compounds encompassed by structural formula (I) are as follows:

Utility and Administration

The compounds defined by structural formula (I) are useful as antiandrogenic agents and are therefore useful for the treatment of clinical conditions that are androgen-responsive and/or associated with androgen excess, such as prostate carcinoma, benign prostatic hyperplasia, acne, seborrhea, alopecia, hirsutism, polycystic ovarian disease, and male pattern baldness. The compounds may be conveniently formulated into pharmaceutical compositions composed of one or more of the compounds in association with a pharmaceutically acceptable carrier. Remington's Pharmaceutical Sciences, latest edition, by E. W. Martin (Mack Publ. Co., Easton Pa.) discloses typical carriers and conventional methods of preparing pharmaceutical compositions which may be used to prepare formulations using the antiandrogenic compounds of the invention. The compounds may also be administered in the form of pharmacologically acceptable salts or esters. Salts or esters of the compounds may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992), the disclosure of which is hereby incorporated by reference. Preparation of esters would normally include functionalization of the steroid molecule at the C-17 hydroxyl group, e.g., to incorporate a succinate, malonate, glutarate group or the like.

The compounds may be administered orally, parenterally (e.g., intravenously), topically, transdermally, by intramuscular injection, or by intraperitoneal injection, or the like, although oral administration is preferred. The amount of active compound administered will, of course, be dependent on the subject being treated, the subject's weight, the manner of administration and the judgment of the prescribing physician. Generally, however, dosage will be in the range of approximately 0.5 mg to 20 mg/kg/day, more typically in the range of about 1.0 mg to 10 mg/kg/day.

Depending on the intended mode of administration, the pharmaceutical compositions may be in the form of solid, semi-solid or liquid dosage forms, such as, for example, tablets, suppositories, pills, capsules, powders, liquids, suspensions, or the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

Process for Preparation

The compounds of the invention may be prepared in high yield using relatively simple, straightforward methods as exemplified in the experimental section herein.

Synthesis of representative compounds are detailed in the examples as follows. Synthesis of compound II-1 is described in detail in Example 1, while synthesis of compound III-1 is described in detail in Example 2.

Biological testing procedures and results are set forth in Example 3.

Experimental

The practice of the present invention will employ, unless otherwise indicated, conventional techniques of synthetic organic chemistry, biological testing, and the like, which are within the skill of the art. Such techniques are explained fully in the literature. See, e.g., Fieser et al., *Steroids* (New York: Reinhold, 1959), and Djerassi, *Steroid Reactions: An Outline for Organic Chemists* (San Francisco: Holden-Day, 1963), for detailed information concerning steroid-related synthetic procedures, and *J. Steroid Biochem.* 12:143–157 (1980), for a description of steroid hormone receptor competition assays useful to evaluate compounds such as those described and claimed herein. All patents, patent applications, and publications mentioned herein, both supra and infra, are hereby incorporated by reference.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to insure accuracy with respect to numbers used (e.g., amounts, temperature, etc.) but some experimental error and deviation should be accounted for. Unless indicated otherwise, temperature is in degrees C and pressure is at or near atmospheric. All solvents were purchased as HPLC grade, and all reactions were routinely conducted under an inert atmosphere of argon unless otherwise indicated. NMR analyses were conducted on either a Varian XL-400 or a JEOL FX90Q and were referenced to chloroform at δ 7.27. FTIR spectra were recorded on a Perkin-Elmer 1610.

Example 1
Scheme 1

This example describes synthesis of 17α-propylestra-4,9-dien-17β-ol-3-one (II-1), as illustrated in Scheme 1.

(a.) 3-Methoxy-17α-propynylestra-1,3,5-trien-17β-ol (2)

To a solution of 3-methoxyestrone (1; 9.02 g, 31.8 mmol) in THF (250 mL) was added a solution of propynylmagnesium bromide (120 mL of 0.56M in THF). The resultant yellow solution was heated at reflux for 3 hours, then allowed to cool to ambient temperature, stirred with saturated aqueous NH$_4$Cl (100 mL) and extracted with ethyl acetate (3×100 mL). The combined organic layers were washed with brine (2×100 mL), dried over MgSO$_4$ and evaporated to give a yellow solid, which was recrystallized from a mixture of ethyl acetate and hexane to provide white microcrystals, 8.77 g (85%), mp 199°–200° C.

NMR (90 MHz, CDCl$_3$): δ 0.94 (s, 3H, CH$_3$), 1.10–2.54 (m, 16H), 2.72–3.08 (bm, 3H), 3.84 (S, 3H, OCH$_3$), 6.70–6.85 (M, 2H, ArH), 7.05 (d, 1H, J=3.6 Hz, ArH). IR (Nujol): 3500, 1610 cm$^{-1}$. MS: m/q (rel int) 324 (100), 243 (40), 227 (47), 174 (42). HRMS. Calculated for C$_{22}$H$_{28}$O$_2$: 324.209. Found: 324.210.

(b.) 3-Methoxy-17α-propylestra-1,3,5-trien-17β-ol (3)

A suspension of alkyne 2 (4.00 g, 12.3 mmol), 5% Pd/C (100 mg), and ethyl acetate (400 mL) was stirred under an atmosphere of H$_2$ for 14 hours. The catalyst was filtered off and the filtrate was concentrated in vacuo to provide a white foam, which crystallized from methanol in successive crops to afford 3.70 g (92%) of white needles, mp 96°–970° C.

NMR (90 MHz, CDCl$_3$): 0.95 (s, 3H, CH$_3$), 0.99–2.45 (m, 19H), 2.70–3.05 (m, 3H), 3.82 (s, 3H, OCH$_3$), 6.60–6.84 (m, 2H, ArH), 7.20 (d, 1H, J+3.8 Hz, ArH). IR (Nujol): 3520, 1610 cm$^{-1}$. MS: m/q (rel int) 328 (100), 247 (35), 227 (48). HRMS. Calculated for C$_{22}$H$_{32}$O$_2$: 328.240. Found: 328.240.

(c.) 3-Methoxy-17α-propylestra-2,5(10)-dien-17β-ol (4)

To liquid ammonia (350 mL) at −78° C. was added lithium shot (0.63 g). After the metal had dissolved, dry isopropanol (30 mL) and a solution of aromatic 3 (4.70 g, 14.3 mmol) in THF (100 mL) was added in succession. After 30 minutes at −78° C., the resultant blue solution was allowed to warm to ambient temperature overnight. The resultant cloudy solution was stirred with saturated aqueous ammonium chloride (200 mL) and diethyl ether (200 mL). The ethereal layer was separated, washed with saturated aqueous ammonium chloride (100 mL) and brine (2×100 mL), dried over K$_2$CO$_3$ and evaporated to afford a white amorphous solid, 4.90 (100%) which was routinely used without further purification and crystallized from a mixture of diethyl ether and hexane to give analytical pure crystals, mp 148°–149° C.

NMR (90 MHz, CDCl$_3$): δ 0.78–2.60 (m, 27H), 2.50–2.80 (m, 3H), 3.55 (s, 3H, OCH$_3$), 4.68 (m, 1H). IR (Nujol): 3500 cm$^{-1}$. MS: m/q (rel int) 330 (100), 122 (97). HRMS. Calculated for C$_{22}$H$_{34}$O$_2$: 330.256. Found: 330.256.

(d.) 17α-Propylestra-5(10)-en-17β-ol-3-one (5)

To a solution of enol ether 4 (3.00 g, 9.10 mmol) in THF (100) mL) and methanol (100 mL) was added a solution of oxalic acid (4.0 g) in H$_2$O (40 mL). After 60 minutes at ambient temperature, a small amount of K$_2$CO$_3$ was added, and the resultant solids were dissolved with a minimal amount of H$_2$O. The mixture was extracted with diethyl ether (3×100 mL). The combined ethereal layers were washed with H$_2$O (50 mL) and brine (2×50 mL), dried over Na$_2$SO$_4$ and evaporated to a white amorphous solid, which recrystallized from diethyl ether/ethyl acetate/hexane in successive crops to give white crystals, 2.76 g (96%), mp 148°–149.5° C.

NMR (90 MHz, CDCl$_3$): δ 0.94 (2, 3H, CH$_3$), 0.95–2.20 (m, 23H), 2.45 (bs, 4H), 2.75 (bs, 2H). IR (Nujol): 3440, 1705 cm$^{-1}$. MS: m/q (rel int) 316 (100), 298 (47), 230 (100). HRMS. Calculated for C$_{21}$H$_{34}$O$_2$: 316.240. Found: 316.240.

(e.) 17α-propylestra-4,9-dien-17β-ol-3-one (II-1)

To a solution of γ-enone 5 (398 mg, 1.26 mmol) in pyridine (30 mL) was added pyridine hydrobromide perbromide (0.60 g, 1.6 equivalent). After 2 hours at ambient temperature, the reaction mixture was stirred with 10% aqueous HCl (150 mL) and extracted with diethyl ether (3×25 mL). The combined ether layers were washed with 10% aqueous HCl (10 mL), brine (2×10 mL), saturated aqueous NaHCO$_3$ (2×25 mL), saturated aqueous CuSO$_4$ (15 mL) and brine (2×15 mL), dried over Na$_2$SO$_4$ and evaporated to give a yellow oil, which was further purified via flash column chromatography with silica gel. Elution with a mixture of ethyl acetate and hexane led to isolation of diene II-1 as a colorless foam, 249 mg (63%).

NMR (90 MHz, CDCl$_3$): δ 0.75–3.20 (m, 29H), 5.65 (s, 1H). IR 3450, 2960, 2880, 1670, 1600, 1370, 1280, 1250, 1210, 1010, 740 cm$^{-1}$. MS: m/q (rel int) 314 (82), 228 (100), 215 (97). HRMS. Calculated for C$_{21}$H$_{30}$O$_2$: 314.225. Found: 314.225. UV (ethanol): λmax 306 nm (ε=20, 740).

Example 2
Scheme 2

-continued
Example 2
Scheme 2

This example describes preparation of 2',3'α-tetrahydrofuran-2'-spiro-17-(5α-androstan[2,3-c]furazan (III-1).

(a.) 2-Hydroxyimino-17β-hydroxy-5α-androstan-3-one (7)

To a solution of steroid 6 (17β-hydroxy-5α-androstan-3-one) in benzene/methanol was added a mixture of HCl and methanol. To this solution with vigorous stirring was added t-BuNO₂ in benzene. During the addition the reaction temperature was kept between 19 and 25° C. Also, on addition of the t-BuNO₂, a precipitate appeared after completion of the addition, and the reaction was stirred for an additional 1 hour at room temperature. 20 mL of H₂O was added and the resulting precipitate was collected and washed with H₂O, 2% NaHCO₃ and H₂O. After drying, there was obtained 29.3 g of crude product 7, which was recrystallized from methanol to give 24.22 g purified product. Mp 264–266 dec., lit. mp=266–267 dec.

(b). 17β-Acetoxy-2,3-dihydroxyimino-5α-androstane (8)

A suspension of steroid 7, NH₂OH.HCl and NaOAc/H₂O was refluxed for 20 minutes. The reaction was cooled to room temperature and poured into H₂O. The precipitate was collected by filtration. The resulting solid 8 was washed with H₂O and air and dried; wt. 23.4 g.

(c.) 17β-Hydroxy-5α-androstan[2,3-c]furazan (9)

A suspension of steroid 8 and KOH in ethylene glycol was heated to 180°–190° C. for 0.5 h. During this time the steroid dissolved. The reaction mixture was cooled and then poured into H₂O. The solid was collected by filtration and washed with H₂O. The solid was dissolved in CHCl₃, dried over Na₂SO₄ and evaporated at reduced pressure, wt. 7.49 g. Purification by dry column chromatography CHCl₃/10% ethyl acetate gave 3.30 g of pure product 9. Recrystallization from 95% ethanol yielded 2.55 g; Mp 157°–159° C.; lit. mp 160°–161° C.

(d.) 17-Keto-5α-androstan[2,3-c]furazan (10)

To a solution of alcohol 9 (1.4 g, 4.43 mmol) in acetone (70 mL) was added dropwise Jones reagent until an orange color persisted. TLC at this time showed no starting matter present. The reaction mixture was diluted with water (200 mL). The crude material was taken up on a filter and washed with water. The crude material was dried under vacuum overnight, and was chromatographed on a silica gel column that was eluted with 5% ethyl acetate, 10% hexane in dichloromethane. Yield of pure 10, 1.19 g (85.5%).

(e.) 17β-hydroxy-17α-tetrahydropyranyl-oxypropargyl-5α-androstan[2,3-c]furazan (11)

To a solution of ethyl magnesium bromide (3.16 mL of 3.0M in ether, 2.5 equivalent) in THF (10 mL) at –78° C. was added via syringe the tetrahydropyranyl ether of propargyl alcohol (1.47 mL. ~2.6 equivalent). The resultant slurry was allowed to warm to room temperature over 1 hour when a solution of ketone 10 (1.19 g, 3.79 mmol) in THF (15 mL) was added via cannula. Only traces of starting material remained after 10 minutes. After 8 hours of stirring at room temperature, the reaction mixture was stirred with saturated aqueous ammonium chloride solution (100 mL) and extracted with CH₂Cl₂ (3×50 mL). The combined organic layers were washed with saturated NaCl, dried over K₂CO₃, and evaporated to give 2.47 g of a yellow oil, which was purified on a silica gel column and eluted with 10% ethyl acetate/10% hexane in CH₂Cl₂ to afford 1.72 of desired product 11 (~100% yield).

(f.) 17β-hydroxy-17α-(3'-tetrahydropyranyl-oxypropyl)-5α-androstan[2,3-c]furazan (12)

To a solution of 11 (1.72 g, 3.79 mmol) in ethyl acetate (100 mL) was added 5% Pd/C (100 mg) and this solution was hydrogenated at atmospheric pressure. After 13 hours, no starting material was present, but some olefin remained. Some fresh catalyst was added, but no further changes were observed after another 2 hours. The catalyst was filtered off and the filter was washed with ethyl acetate (100 mL). The filtrate was evaporated to a white foam. Yield 1.61 g crude 12.

(g.) 17β-Hydroxy-17α-(3'hydroxypropyl)-5α-androstan[2,3-c]furazan (13)

To a solution of 12 (crude 1.6 g, 3.49 mmol) in methanol (100 mL) was added p-toluenesulfonic acid (0.72 g, 1.1 equivalent). After 30 minutes of stirring at room temperature, TLC showed complete reaction. The reaction solution was stirred with saturated aqueous sodium bicarbonate solution (100 mL) and CH₂Cl₂ (100 mL). The resultant suspension was poured into water (50 mL). The aqueous solution was extracted with CH₂Cl₂ (2×100 mL). The combined CH₂Cl₂ was washed with saturated sodium chloride solution (50 mL), dried over potassium carbonate and evaporated 1.22 g of white solid. NMR was in agreement with proposed structure 13.

(h.) 2',3'α-Tetrahydrofuran-2'-spiro-17-(5α-androstan[2,3-c]furazan (III-1)

To a solution of diol 13 (1.22 g, 3.26 mmol) in pyridine (100 mL) was added p-toluenesulfonyl chloride (2.0 g; 3.2 equivalent) under argon. Stirring at room temperature for 16 hours gave the desired product III-1. The reaction mixture was stirred with saturated aqueous sodium bicarbonate solution (150 mL) for 10 minutes. The resultant suspension was treated with water and extracted with ether (3×100 mL). The combined ether layers were washed with sodium bicarbonate solution and NaCl solution, dried over potassium carbonate, and evaporated to give 0.98 g of crystalline material. Purification of III-1 by column chromatography gave 0.39 g of white plates, mp 152°–153° C. The structure was confirmed by NMR, UV and IR spectroscopy.

EXAMPLE 3

Biological Evaluation

Preparation of Cytosol

Male rats were gonadectomized 20–22 hours before killing. The animals were killed by decapitation and exsanguination. Prostates were kept on ice immediately after removal from the animals. After trimming off the fats, prostates were minced and homogenized in 3 volumes of Tris-HCl buffer (0.02M, pH 7.4 containing 1.5 mM EDTA and 10% glycerol). The homogenate was centrifuged at 10,000×g for 10 minutes, and the resulting supernatant was centrifuged again at 100,000×g for 60 minutes. The final supernatant contained the androgen-binding receptor.

Labeling of Receptor Proteins

For the binding assay, 0.75 mL of prostate cytosol was mixed with 5 µL of DMSO containing 0.09 ng, 27500 dpm of $^3$H-dihydrotestosterone and 1 µL of DMSO alone or DMSO plus competitor. The mixture was brought up to 1.0 mL with Tris-HCl buffer used for homogenizing the tissue. The mixture was then incubated at 4° C. for 4 hr., with occasional shaking. At the end of incubation, the receptor-bound androgen was isolated by ammonium sulfate precipitation.

Precipitation of Receptor-Bound Androgen

A 70% saturated ammonium sulfate solution was prepared and its pH is adjusted to 7.4 with aqueous $NH_3$. To 1.0 mL of the labeled cytosol, 1.0 mL of the 70% saturated ammonium sulfate was added dropwise with gentle mixing. The sample was let stand at 0°–4° C. for 35 minutes, then centrifuged at 10,000×g for 20 minutes. The precipitate was resuspended in 1.0 mL of the above-mentioned Tris-HCl buffer containing 2 mg of bovine albumin. The androgen-receptor complex was immediately reprecipitated by addition of equal volumes of 70% saturated ammonium sulfate. The sample was allowed to stand at 0°–4° C. for another 45 minutes, then centrifuged again as outlined above. The supernatant was decanted and the walls of the tubes thoroughly dried with filter paper. The final precipitated protein was resuspended in 1.0 mL of the same buffer and then transferred quantitatively into a counting vial containing 10 mL of Scintisol for counting. The androgen-receptor complex precipitated at 35% ammonium sulfate not only separating it from free $^3$H-dihydrotestosterone but also from androgen-binding protein which precipitated at 50% ammonium sulfate, and bovine albumin which precipitated at 60–80% ammonium sulfate.

Comparison of Relative Binding Affinities

In order to compare the relative binding affinities of various antiandrogens reported in the literature, we have extrapolated from reported $IC_{50}$ values of various antiandrogens using dihydrotestosterones (DHT) as the standard and assigned the value of 100. This comparison is illustrated in Table 1. As the table indicates, compounds II-1 and III-1 exhibit a higher affinity for the androgen rat prostate receptor than all of the other known antiandrogens except cyproterone acetate.

TABLE 1

| Rat Prostate Androgen Receptor Competition Assay | |
|---|---|
| Competitor | Relative Binding Affinity[a] |
| 5α-Dihydrotestosterone[b] | 100 |
| Cyproterone Acetate | 17.7 |
| Compound III-1 | 5.8 |
| Compound II-1 | 5.7 |
| Hydroxyflutamide | 2.6 |
| Win 49,596 | 2.2 |
| ICI-176,334-Casodex ® | 2.0 |

[a]RBA = Conc. of 5αDHT at 50% binding inhibition/conc. of competitor at 50% binding inhibition × 100.
[b]Rel. binding affinity set at 100.

Also, it may be seen that compounds II-1 and III-1 display a higher affinity for the rat ventral prostate androgen receptor than the steroidal antiandrogen zanoterone (WIN® 49,596). Compounds II-1 and III-1 bind with higher affinity to the androgen receptor than three other nonsteroidal antiandrogen receptor antagonists flutamide, which is available as an antiandrogen in the United States, nilutamide, developed by Roussel in France, and Casodex® (ICI 176,334). It is interesting to note that as previously demonstrated with other antiandrogens, the magnitude of androgen receptor binding shows a good correlation with in vivo antiandrogenic potency as measured by their inhibition of prostatic growth in intact male rats.

In the in vivo studies summarized below, evaluating compounds II-1 and III-1 on inhibition of prostate growth in castrated male rats given supplemental testosterone, a similar correlation between in vivo potency and androgen receptor binding affinity was apparent, as indicated in Table 3.

Inhibition of Prostate Growth in Castrated Male Rats by Compounds II-1 and III-1

Male rats weighing 36 to 38 grams were castrated at the age of 22 days. On the day of castration, the animals were treated with the agonist, testosterone; 0.6 mg and the antagonists III-1, 30.0 mg; II-1, 30.0 mg; and cyproterone acetate, 30.0 mg was used as the antiandrogenic reference standard. The castrated rats were treated with the steroids once daily for ten consecutive days. On the tenth day following treatment, the rats were sacrificed and autopsied and final seminal vesicle weights and ventral prostate weights determined. The results of the inhibition of prostate growth by compounds II-1 and III-1 and the antiandrogenic reference standard cyproterone acetate are shown in Table 2 below.

TABLE 2

EFFECT OF ANTIANDROGEN ON SEX ACCESSORY GLANDS AND TESTES OF 22-DAY OLD CASTRATED MALE RATS

| | | | Weight (mean ± SE) | | | |
|---|---|---|---|---|---|---|
| Compound | Dose (mg/Day)[+] | "N" | Initial BW (g) | Final BW (g) | Seminal Vesicle (mg) | Ventral Prostate (mg) |
| Vehicle (Sesame oil) | — | 5 | 36 ± 1 | 85 ± 3 | 6.1 ± 0.6 | 10.4 ± 1.1 |
| Testosterone propionate | 0.6 | 5 | 37 ± 2 | 86 ± 4 | 26.6 ± 34 | 53.4 ± 5.8 |
| Cyproterone acetate | 30.0 | | | | | |
| Testosterone propionate | 0.6 | 5 | 35 ± 2 | 76 ± 5 | 9.8 ± 0.8 | 30.0 ± 3.6 |
| II-1 | 30.0 | | | | | |
| Testosterone propionate | 0.6 | 5 | 36 ± 1 | 88 ± 5 | 28.2 ± 2.8 | 45.3 ± 2.5 |
| III-1 | 30.0 | | | | | |
| Testosterone propionate | 0.6 | 3 | 38 ± 1 | 89 ± 5 | 22.5 ± 1.1 | 39.5 ± 4.1 |

These results clearly establish compounds II-1 and III-1 as a new chemical class of steroidal antiandrogens. In vivo they act as competitive androgen receptor antagonists and inhibit prostate growth stimulated by exogenous testosterone in the male castrated rats. The magnitude of prostatic growth inhibition also appears to be dose dependent, as shown in Table 4, but this tentative conclusion must await further experimental dose/response studies for final confirmation.

Relative in vivo antiandrogenic potencies are as follows:

TABLE 3

| | In Vivo Percent Inhibition of Androgen Receptor | In Vivo Relative Ventral Prostate Affinity Weight |
|---|---|---|
| Cyproterone acetate | 54.3 ± 8.34 | 17.7 |
| Compound III-1 | 32.2 ± 9.49 | 5.8 |
| Compound II-1 | 18.8 ± 5.74 | 5.7 |
| Hydroxyflutamide | | 2.6 |

TABLE 3-continued

| | In Vivo Percent Inhibition of Androgen Receptor | In Vivo Relative Ventral Prostate Affinity Weight |
|---|---|---|
| Zanoterone | | 2.2 |
| Casodex ® | | 2.0 |

Effect of Different Doses of Antiandrogen Compound III-1 on Sex Accessory Glands and Testes of Intact Sprague-Dawley Male Rats The foregoing procedures were used to evaluate the effect of antiandrogen compound III-1 on the sex accessory glands and tests of intact Sprague-Dawley male rats. Results are set forth in Table 4. As may be seen in the Table, ventral prostate growth after administration of the antiandrogen than after administration of the control (sesame oil), indicating antagonism on the effect of the testosterone produced.

TABLE 4

EFFECT OF ANTIANDROGEN ON SEX ACCESSORY GLANDS AND TESTES OF INTACT SPRAGUE-DAWLEY MALE RATS

| | | | Weight (mean ± SE) | | | | |
|---|---|---|---|---|---|---|---|
| Compound | Dose (mg/day)[a] | "N" | Body Weight (g) | Seminal Vesicle (mg) | Ventral Prostate (mg) | Epididymus (mg) | Testes (g) |
| Vehicle (Sesame oil) | | 4 | 312 ± 8 | 628 ± 65 | 431 ± 61 | 954 ± 39 | 3.184 ± .145 |
| III-1 | 10 | 4 | 295 ± 5[b] | 225 ± 40[c] | 170 ± 13[d] | 524 ± 48[e] | 2.552 ± 111[f] |
| III-1 | 30 | 4 | 277 ± 9[g] | 242 ± 61[c] | 148 ± 28[d] | 458 ± 39[e] | 1.942 ± .062[e] |

[a] Administered subcutaneously once daily for 12 days
[b] Not statistically different from control.
[c] Statistically lower than control, P < .005.
[d] Statistically lower than control, P < .01.
[e] Statistically lower than control, P < .001.
[f] Statistically lower than control, P < .02.
[g] Statistically lower than control, P < .05.

The lack of agonist androgenic activity in the competitive receptor binding antagonists II-1 and III-1 was demonstrated in vivo by the standard Hershberger androgenic assay conducted with 22 day old castrated male rats. The seminal vesicle and ventral prostate weights of the animals treated with II-1 and III-1 at doses of 0.8 mg, 1.6 mg, and 3.2 mg were equal to the vehicle alone controls. Very flat dose response curves for androgenic activity were obtained, indicating by extrapolation that at the therapeutically effective antiandrogenic dose in the castrated male rat (30.0 mg), both III-1 and II-1 are essentially devoid of agonist androgenic activity.

Figure 1:
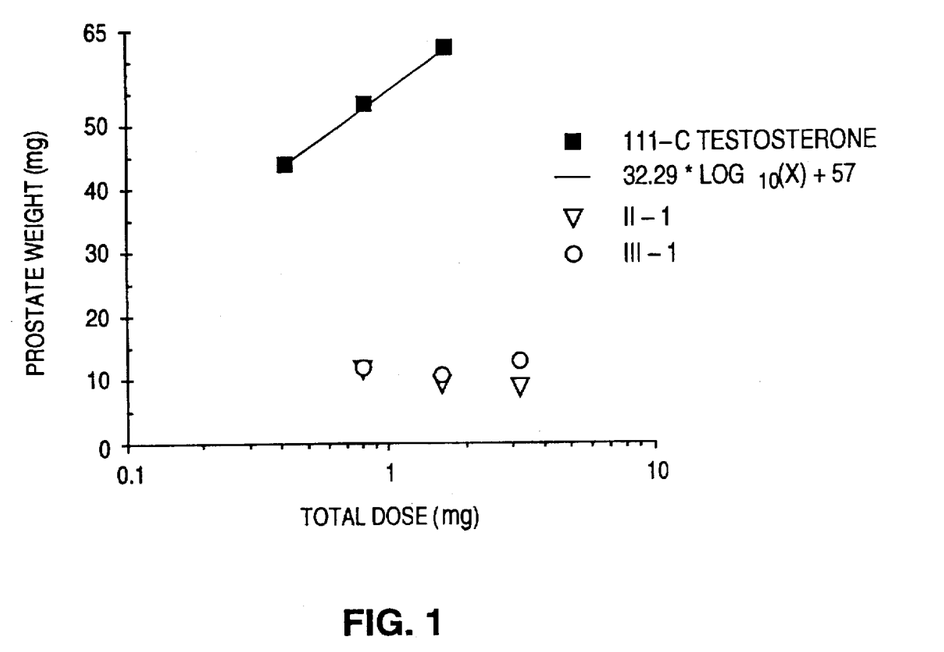
FIG. 1 is a graph illustrating the effect of drug dosage on prostate weight, as explained in Example 3.

FIG. 1 clearly demonstrates that compounds II-1 and III-1 provide for a fairly steady prostate weight, even at higher doses. By comparison, it may be seen that testosterone itself causes a proportionate rise in prostate weight with increasing dose.

Measurement of Prostatein $C_3$ mRNA

The assay set forth in *The Prostate* 17:41 (1990), was followed to evaluate the androgen responsiveness of rat ventral prostate explant cultures to compound III-1 combined with dihydrotestosterone. Testosterone was used as a control. As explained in the aforementioned reference, the test makes use of prostatein, an androgen-dependent protein secreted by the rat ventral prostate. Addition of androgens to the medium of rat prostate explant cultures maintains the mRNA for $C_3$ subunit of prostatein, and measurement of either prostatein or its $C_3$ subunit mRNA serves as a sensitive, androgen-responsive marker for the explant system. Results are set forth in Table 5:

TABLE 5

RAT VENTRAL PROSTATE EXPLANT CULTURE-III-1

| | N (30 disks/ explant) | C3 m-RNA (30 disks/ explant) | C3*/28s × 100 |
|---|---|---|---|
| Control | 3 | 0 | 0 |
| Dihydrotestosterone (25 nM) | 3 | 219,371 (100%) ± 32,675 | 148.9 (100%) ± 26.9 |
| Dihydrotestosterone (25 nM)/III-1 (2500 nM) combination | 2 | 95,130 (43%) ± 1,603 | 91.8 (62%) ± 0.8 |

*C3 = C3 subunit of prostatein.
28S = 28S ribosomal RNA (total RNA)

As may be seen in Table 5, prostatein and subunit mRNA fall dramatically following castration, indicating marked antiandrogenic activity of the compound III-1/dihydrotestosterone formulation.

Additional In Vivo Studies

An additional in vivo protocol which may be followed to evaluate the efficacy of the novel compounds involves the androgen-sensitive PAP variant of the Dunning R-3327 prostatic carcinoma in male Copenhagen x Fischer, $F_1$ rats. Flutamide, nilutamide or the like may be used as a positive control, administered, like the novel compounds, by oral gavage and SC sesame oil suspension. Tumored rats may be tested once the tumors become measurable, generally 7–20 weeks from implantation. Three treatment groups will be given 20, 60 and 200 mg(sc)/kg/day, a fourth treatment group will be given 100 mg p.o./kg/day, and a fifth, control group will be given 30 mg(sc)/kg/day flutamide or a similar dose of nilutamide or the like. Rats will receive a single daily dose either sc or oral gavage for 28 days and will be weighed weekly. Tumors will be measured in three planes twice a week. Tumor volume doubling time and ventral prostate weights will be evaluated. It is expected that the compounds of the invention will reduce tumor volume doubling time significantly and keep ventral prostate weight relatively low.

We claim:

1. A compound having the structural formula wherein:

$R^1$ and $R^2$ are independently selected from the group consisting of hydrogen and lower alkyl; and one of $R^6$ and $R^7$ is hydroxyl and the other is n-propyl, or $R^6$ and $R^7$ are linked to provide a cycloalkyl group containing 3 to 6 carbon atoms.

2. The compound of claim 1, wherein $R^1$ and $R^2$ are both hydrogen.

3. The compound of claim 2, wherein one of $R^6$ and $R^7$ is hydroxyl and the other is n-propyl.

4. The compound of claim 3, having the structural formula (II-1)

5. The compound of claim 1, wherein one of $R^6$ and $R^7$ is hydroxyl and the other is n-propyl.

6. The compound of claim 1, wherein $R^6$ and $R^7$ are linked to provide a cycloalkyl ring of 3 to 6 carbon atoms.

7. A pharmaceutical composition comprising, in combination with a pharmaceutically acceptable carrier, an amount of a compound having the structural formula wherein:

$R^1$ and $R^2$ are independently selected from the group consisting of hydrogen and lower alkyl; and one of $R^6$ and $R^7$ is hydroxyl and the other is n-propyl, or $R^6$ and $R^7$ are linked to provide a cycloalkyl group containing 3 to 6 carbon atoms.

8. The composition of claim 7, wherein $R^1$ and $R^2$ are both hydrogen.

9. The composition of claim 8, wherein one of $R^6$ and $R^7$ is hydroxyl and the other is n-propyl.

10. The composition of claim 9, wherein the compound has the structural formula (II-1)

11. The composition of claim 7, wherein one of $R^6$ and $R^7$ is hydroxyl and the other is n-propyl.

12. The composition of claim 7, wherein $R^6$ and $R^7$ are linked to provide a cycloalkyl ring of 3 to 6 carbon atoms.

13. A compound having the structural formula wherein:

$R^5$ is hydrogen or lower alkyl; and $R^6$ and $R^7$ are linked to provide a cycloalkyl or cyclooxyalkyl ring containing 3 to 6 carbon atoms.

14. The compound of claim 13, wherein $R^5$ is methyl.

15. The compound of claim 14, wherein $R^6$ and $R^7$ are linked to provide a cyclooxyalkyl ring containing 3 to 6 carbon atoms.

16. The compound of claim 15, having the structural formula

17. The compound of claim 13, wherein $R^6$ and $R^7$ are linked to provide a cyclooxyalkyl ring containing 3 to 6 carbon atoms.

18. A pharmaceutical composition comprising, in combination with a pharmaceutically acceptable carrier, an amount of a compound having the structural formula wherein:

$R^5$ is hydrogen or lower alkyl; and $R^6$ and $R^7$ are linked to provide a cycloalkyl or cyclooxyalkyl ring containing 3 to 6 carbon atoms.

19. The composition of claim 18, wherein $R^5$ is methyl.

20. The composition of claim 18, wherein $R^6$ and $R^7$ are linked to provide a cyclooxyalkyl ring containing 3 to 6 carbon atoms.

21. The compound of claim 20, having the structural formula

22. The composition of claim 18, wherein $R^6$ and $R^7$ are linked to provide a cyclooxyalkyl ring containing 3 to 6 carbon atoms.

* * * * *